United States Patent [19]

Zöld

[11] Patent Number: 4,954,715

[45] Date of Patent: Sep. 4, 1990

[54] METHOD AND APPARATUS FOR AN OPTIMIZED MULTIPARAMETER FLOW-THROUGH PARTICLE AND CELL ANALYZER

[76] Inventor: Tibor Zöld, PhilippiStr. 13, 4400 Münster, Fed. Rep. of Germany

[21] Appl. No.: 474,628

[22] Filed: Jan. 29, 1990

Related U.S. Application Data

[63] Continuation of Ser. No. 372,232, Jun. 26, 1989, abandoned, which is a continuation of Ser. No. 598,151, Apr. 9, 1984, abandoned.

[51] Int. Cl.$^5$ .................. G01N 21/64; G01N 21/05
[52] U.S. Cl. .................. 250/461.1; 250/461.2; 356/338; 356/246
[58] Field of Search .................. 250/461.1, 461.2, 441, 250/442; 356/338, 246

[56] References Cited

U.S. PATENT DOCUMENTS

| | | | |
|---|---|---|---|
| 3,738,759 | 6/1973 | Dittrich et al. | 356/442 |
| 4,175,662 | 11/1979 | Zöld | 209/552 |
| 4,225,229 | 9/1980 | Göhde | 250/461.2 |
| 4,237,416 | 12/1980 | Zöld | 324/71.1 |
| 4,352,558 | 10/1982 | Aisert | 250/461.2 |
| 4,515,274 | 5/1985 | Hollinger et al. | 356/246 |

FOREIGN PATENT DOCUMENTS

57-153248  9/1982  Japan .................. 356/246

*Primary Examiner*—Janice A. Howell
*Assistant Examiner*—Richard Hanig
*Attorney, Agent, or Firm*—Toren, McGeady & Associates

[57] ABSTRACT

The invention discloses a method, device, and apparatus of very high reliability and stability for the multiparameter analysis of particles and cells in suspension. The very high reliability and stability of these devices follows from the fact that the various cavities, channels, and holes join everywhere at very small angles and therefore the joining or rejoining of the various liquids flowing in the device occurs with practically zero turbulence, and that nowhere in the flow-system do air bubbles get trapped because sharp edges and corners are eliminated everywhere within said system. From the fact that the cavities, channels, and holes join at small angles and are of short length follows that the cleaning and maintenance of said device is also very easy because the said character of said cavities, etc., permits a direct, visual observation of any point of the inside of said flow-system and an easy reaching for cleaning purposes of any part of it, from where it follows that the routine work with this type of particle analyzer is extremely easy. Three different UV-light sources are combinable to this type of analyzer apparatus which extends the applicability of said apparatus beyond that of the conventional models. The sensitivity of this analyzer type is about ten times higher than that of the jet type frequently used nowadays in cytological research. The said analyzer device is readily combinable with a cell or particle sorter device, such as described in U.S. Pat. No. 4,175,662, so its application can be extended to cell or particle sorting, too.

22 Claims, 2 Drawing Sheets

METHOD AND APPARATUS FOR AN OPTIMIZED MULTIPARAMETER FLOW-THROUGH PARTICLE AND CELL ANALYZER

This is a continuation application of Ser. No. 07/372,232, filed June 26, 1989, which in turn is a continuation application of Ser. No. 06/598,151, filed Apr. 9, 1984 both now abandoned.

CHARACTER AND FIELD OF APPLICATION

This invention relates to a high stability and reliability multiparameter flow-through cell or particle analyser and the method and means by which in this analyser a stable and thin center-stream is constrained by another stream, called the sheath-stream, which envelops completely said center-stream, to flow at the center of a small tube or channel of capillary size, and in which the nozzle chamber, wherein said streams are combined, has such an inside wall geometry that the said sheath-stream envelops at any time of operation the said tube without any turbulence and air bubbles generation, before said sheath-stream reaches said center-stream emanating from the said small tube; the said center-stream carries the particles or cells to the volumes of analysis where the cells interact through some of their physico-chemical properties with a number of sensors each. The result of such an interaction is an electrical voltage and/or current impulse in the electronic system of each sensor which is further analysed by other electronical equipments connected to the particular sensor. (One typical equipment used here is the multichannel analyser which is capable of displaying and recording the number of particles vs. the magnitude of the physical quantity which is analysed by the sensor. For instance, if the quantity is the cell volume then said multichannel analyser gives the distribution of the cell volume in a cell suspension.)

Sensors are usually of optical nature which involve a UV-microscope objective in order to collect the light which is scattered from or emitted by the fluorescent dyeing of the cell and illuminated by the excitation light in the UV-spectrum; presently there is known only one type of electrical sensor for the sizing of the particles. The volume of analysis by optical sensors (equal to the product of the sight-field and the focal depth) is very often rather small and/or inhomogeneous. Therefore the center-stream has to be very stable at any moment of the operation of the analyser as the cells are passing, one after the other, through said volume of analysis. Consequently, this invention relates also to an improved nozzle chamber, where the center and sheath-stream combination is generated without causing any turbulence and air bubbles and therefore an extremely stable and reliable center-stream is produced in said chamber from where, in turn, follows the high reliability and stability of operation of the multiparameter analyser equipment. As the references cited below show, this aspect has not been solved satisfactorily in other devices so far. Additionally, several methods are described here which either improve the quality of operation of said analyser or which make possible the easier maintenance and the operating of the device.

From the above description follows that flow-through cell and particle analysers are used mainly in cytology and inside this field in cancer research; volume analysis is also very important in aerosol research.

BACKGROUND ART

From the work of P. J. Crosland-Taylor (Nature, vol. 171, No. 4340, pp. 37–38, Jan. 3, 1953) it becomes undoubtedly clear that he has constructed the first nozzle chamber in order to obtain a hydrodynamically focussed center-stream in combination with a sheath-stream surrounding the former stream. In his device the sheath-stream liquid is injected quasi radially through two entrance holes at the upper and thus the upstream-end of a cavity of cylindrical shape and vertical axis with a diameter larger than that of the entrance holes; this cavity is called nowadays the nozzle chamber. A suspension of blood cells is injected axially through an injection needle of 0.125 mm diameter and the sheath-stream is formed around the needle (nowadays called the nozzle) and also around the blood stream, forming in this manner the stream combination described above; the flow is directed perpendicularly downwards. With a microscope the hydrodynamically focussed blood cell suspension, i.e. the center-stream, is observed and the cells are counted optically as they scatter a light-bundle focussed upon them. After the counting process the cells and the surrounding sheath-stream leave the nozzle chamber radially through a hole located at the downstream-end of the nozzle-chamber. The center-stream (i.e. blood cells) of a diameter of about 10 micron reported by said author, was found to be wavering by about ±50% around its average position. It is also reported that the center-stream was found to waver even more if only one entrance hole was made for the entrance of the sheath-stream liquid. (Here a difference should be made between the sheath-stream liquid and its converted state in the nozzle chamber.) This instability can be explained in such a manner that the said sheath-stream liquid entering the chamber transfers its momentum to the liquid already present in the chamber, thereby producing a slow rotation of the said sheath-stream in the nozzle chamber approximately around the axis of the latter and as the needle (or nozzle), too, was probably not positioned exactly at the axis of the nozzle chamber, the rotating sheath-stream produced a wavering of the blood stream. The modern, so called "jet type analysers", are constructed in a manner rather similar to that of the early version of the nozzle chamber described above and the complaints about the frequent instabilities of these analysers can be partly due to the characteristic instability of the center stream as explained above in connection with the early version of the nozzle chamber.

Clearly, such wavering of said center-stream is acceptable only if the volume of analysis is large enough, which is the case with objectives of long focal length, i.e. of large focal depth. But as such objectives gather only a small fraction of the scattered or emitted fluorescent light by the cell, therefore the modified nozzle chamber, i.e. that of the jet type, came into use only after the development of high power lasers. In the jet type analyser the nozzle chamber is tapered at its down stream-end into a very short capillary tube with an inside diameter of about 0.1 mm, and if this part of the capillary tube is UV-transparent (down to about 200 nm.) then, in principle, there are two positions where the volume of analysis can be situated. Namely, either in the center of the tube, by adjusting the focal plane of the objective there, or outside the tube where the jet-stream flows in free space in a downward direction. In the volume of analysis, the center-stream, the optical axis of the objective and the laser beam are directed quasi perpendicularly to each other in such a manner that the center-stream lies approximately in the focal plain of said objective. (See: M. A. van Dilla et al., in IEEE Transactions in Nuclear Science, NS-21, pp. 716, 1977.) If the said capillary tube is not transparent, as is the case in the droplet deflection (Fulwyler) sorter (Fulwyler, M. J., Science, vol. 150, pp. 910, 1965), then it is of course only possible to situate the volume of analysis into the open jet-stream. The instability of the stream creates instability not only in the analysis but also in the sorting operation because the perturbation in the jet-stream, caused by the instability, disturbs rather strongly the moment of droplet formation (see: Fulwyler, op. cit.) and hence, the quality of the sorting, too, which is another complaint mentioned frequently by workers in this field. An additional disadvantage of the analyser of the jet type is that it requires the use of high energy lasers. These are rather expensive and bulky, and the complete system requires an optical table in order to be mechanically stable, and its operation, because of the high-energy laser involved, is in some cases under strict safety regulations; therefore the search for an easier alternative with lower energy of illumination and with easier operating conditions is well justified, which means the reduction of the particle analyser to an equipment of the desk-set type.

It is clear that the high energy laser can be replaced by a light-source of lower intensity in the UV-region only if one can replace the objective of long focal length and of less light-gathering capability used in the jet system by another UV-objective that has a higher numerical apperture (about 1.3) and consequently has a light-gathering capability of more than one order of magnitude larger than the former objective. In such a case the cells in the center-stream should flow in a rather shallow channel of about 0.05 to 0.1 mm depth, so that the focal plane of this strong objective can be still adjusted into the center-stream, although the channel is covered by a cover glass of 0.17 mm thickness and the focal distance of the said strong objective is only about 0.24 mm.

Such a system is described by W. Dittrich and W. Göhde in the German Patent No. P 19 19 628.2, but the results of analysis were rather poor because, as follows from the description of the simple nozzle chamber (described above), the center-stream was not stable enough to make each cell flow exactly in the focal plane. Therefore, the said inventors have invented the system according to U.S. Pat. No. 3,738,759, and developed a flow-system where the cells do not flow in the focal plane of the strong UV-objective but perpendicularly to it; the cells are illuminated by a rather inexpensive and easy to operate high-pressure mercury lamp of 100 Watts, with a UV-light component of about 10 mWatts, and by using Koeler's-illumination optics in the epiillumination mode. After traversing the volume of analysis, defined earlier as the product of the sight field of the objective and the focal depth, the cells are washed away rather abruptly by a so called cleaning stream, flowing perpendicularly to the optical axis of said objective, and hence to the said particle-stream, too, into another channel which is the continuation of said channel from where the cleaning stream flows; this channel system is covered by a 0.17 mm thick cover glass and the said second channel serves also as exit-channel for the particle-electrolyte mixture which flows under the effect of a suction pump into a collecting bottle as waste.

Clearly, the said channels and the vertical hole in which the cells flow in the direction of the focal plane, form a flow-system in the shape of a vertical "T". The clear advantage of this system, besides the easier illumination conditions, is that the small wavering of the center-stream does not cause great errors in the analysis of the cells, because the sight field of any objective is rather homogeneous at the vicinity of the optical axis. For this reason one would expect rather good results with this type of analyser. This is, however, not always the case because the sudden 90° joining of the center and sheath-stream combination with the cleaning-stream, defined above, is prone to turbulence at the vicinity of the volume of analysis which can affect the analysis itself. That some workers still get very good results with this type of analyser is probably due to the fact that there exists a region of flow velocity for said streams at which they can join without causing an appreciable turbulence in the volume of analysis. Another disadvantage of the 90° deflection of the center and sheath-stream combination is that if a small thread flows in said stream combination, this thread may not be able to follow said deflection of the streams and will get stuck at the joining volume of the channels, i.e. around the volume of analysis, causing rapid clogging in the said volume while the cells are flowing there, stopping eventually the operation of the analyser completely. That such cloggings happen rather frequently has been known from direct observations both in the said system and in other flow systems. To clean out such devices is often tedious and time consuming, not to mention the strain that ensues for the operator while working with such an unreliable analyser equipment. One more shortcoming of the flow system of W. Dittrich and W. Göhde lies in the fact that due to the turbulent flow described above and due to the bulky nature of the attached nozzle chamber, this analyser can not be readily combined with the cell sorters known to exist at the time being, which is indeed a considerable disadvantage at the time when cell sorting becomes more and more necessary.

There are two more works on cell analysers which should be mentioned for the sake of completeness. One of these is the two-parameter analyser of Severin et al. (see: E. Severin et al. in Cytometry, vol. 3, No. 4, pp. 308–310, 1983) where an argon laser beam is combined to the flow system of W. Dittrich and W. Göhde (see: op. cit.); this laser beam reaches the center-stream, and hence the cells, through a channel cut into the body of the device perpendicularly to the cleaning-exit-channel. No experimental results are given by the authors; however, as the flow system is that of W. Dittrich and W. Göhde, the general performance of this two-parameter analyser must be expected to be the same as that described above in relation with the flow system of W. Dittrich and W. Göhde. Therefore, one important disadvantage of the analyser of Severin et al. is that it can not be combined with one of the known sorter devices, either. The second analyser device is that of H. B. Steen (see: Cytometry, vol. 1, No. 1, pp. 26–31, 1980), where cells or latex beads are syringed from a jet of a center and sheath-stream combination to the top side of a microscope glass, illuminated in the epi-illumination mode, and the fluorescent light is collected by a UV-objective of relatively low magnification, located under the cover glass at that point where the jet, and hence the particles fall upon the cover glass. The results are excellent with beads of 1.5 micron and with cells of about 10 micron diameter; however, this type of device can not be combined with a sorter, either, and it is very probable that the said jet is as unstable as those of the previously described jet-analysers, because in said analyser the same type of nozzle chamber is used as in the former ones.

Presently there exists only one type of electrical analyser or sensor in practical use. In its original version, invented by W. H. Coulter, in the middle 1950s (see: van Dilla et al., op.cit.), it was used to count particles passing from a large container into another large container through an orifice with a crossection only slightly larger than that of the cell or particle to be analysed, according to its size. Both containers are filled with electrolyte; in the upstream container the electrolyte also contains the particles or cells to be analysed; in the other container are the cells which were already analysed. Electrodes connect this system to an electrical circuit and as most of the resistance of the electrical circuit is concentrated in the orifice, the passage of a cell or of a nonconducting particle through the orifice causes a sudden increase in the resistance of the liquid system, causing consequently an electrical voltage and/or current impulse in the connected electrical circuit. In a more modern version (see: U. Zimmermann et al., in Bioelectrochemistry and Bioenergetics, vol. 3, pp. 58–83, 1976) the cells are confined into a hydrodynamically focussed center-stream which is surrounded by a particle-free enveloping electrolyte, and are passing through the center of the orifice where the electrical field is to a very high degree uniform. In this manner an accurate sizing of the cells is possible because, as was found out experimentally, the amplitude of the electrical impulse is proportional to the cell (particle) volume. In both said versions, however, the cells are lost after passing through the orifice and hence they are not identifyable for further processings, such as cell sorting. In order to make such a processing possible, too, a flow-system has been developed (see: T. Zöld, U. S. Pat. No. 4,237,416, 1980) where the cells flow in a closed channel system in the center-stream through a very narrow part of the channel system, used here as the orifice, and thus, they are analysed according to their volume and are capable to continue to flow in the same center-stream towards the sorter-part mentioned above (see: T. Zöld, U.S. Pat. No. 4,175,662, 1972) which is also incorporated into the same device body as said analyser, in order to be sorted on the basis of the same quantity. Experiments with such systems provided excellent results even in combination with an optical sensor containing a large UV-objective, i.e. an objective of large numerical apperture and magnification, with epi-illumination using Koeler's-illumination system, in order to provide uniform illumination of the sight field of said UV-objective. A version of such a system is shown in FIG. 2 of U.S. Pat. No. 4,175,662, combined with a sorter system; the hydrodynamical focussing part of the system according to FIG. 2 is described below in greater detail because of its close relation to the system described in this specification. The hydrodynamical focussing, and hence the generation of the center-stream of said FIG. 2, called suspensionstream in the description of FIG. 2 takes place in the nozzle chamber 42, mentioned in said description as "entrance channel". The center-stream liquid flows into said nozzle chamber 42 through a very small capillary tube 44 which ends in nozzle 46. At this position the center-stream liquid comes into contact with the sheathstream liquid in container 48 and flows to the device through a flexible silicon pipe (indicated in said description and in FIG. 2 as number 42, too); the sheath-stream liquid enters the nozzle chamber 42 through a hole of a few mm length which is directed almost perpendicularly to the small tube 44 or nozzle 46; this hole is indicated only with a circle at the high stream end of the nozzle chamber 42, i.e. where the small tube 44 enters said nozzle chamber 42. Because of this geometry the small tube presents itself as an obstacle in the way of the flow of the sheath-stream liquid. Indeed the small tube splits the liquid into three parts. One takes an approximately 90° turn and flows under the small tube 44 towards the tip of the nozzle 46 and the other two parts flow half-way around the said small tube and meet, with a head-on collision, at the top side of the small tube. Then these two stream-parts deflect each other by 90° and both flow towards the nozzle 46 where the three stream parts join again and form the sheath-stream which envelops the center-stream emanating from the nozzle 46. This center and sheath-stream flow-combination, after passing the orifice 28, joins the two side streams flowing into the main channel through 36 and 37, as described in the text of FIG. 2. In this connection the following facts are of interest: Several flow-systems of this type were built and all were functioning in the same way. That is, when the nozzle chamber 42 was air bubble free, a very stable center-stream of high quality was obtained; by introducing hydrodynamical resistance into the flow of the center-stream liquid, center-stream diameters as small as one micron could be obtained which did not waver even when observed through a stereo microscope of a 50-fold magnification; the center-stream was dyed in these cases with black ink in order to make it distinguishable from the surrounding sheath-stream. However, an air bubble free nozzle chamber was achieved only after many startings, i.e. fill-up's, because usually an air bubble developed at that part of the nozzle chamber where the small tube 44 enters the said nozzle chamber 42 and that usually in the starting phase, i.e. when the empty channel system is being filled up with electrolyte under the suction effect of a suction pump attached through buffer bottles and silicon pipes to the exit holes of the flow-system. These air bubbles were found to be of varying size and are clearly caused by and during the head-on collision of said two stream parts of the sheath-stream liquid as the latter enters the empty nozzle chamber and as said stream parts are deflected towards the exit of said chamber, i.e. towards the orifice 28. As such air bubbles change the position and the shape of the center-stream and can even make the latter unstable, the reliability of this flow-system is very poor and this relative defficiency renders it to be only marginally useful for clinical practice where equipment of stable and high reliability is needed in order to obtain fast and reliable diagnostics.

From the described BACKGROUND ART result the following conclusions: Large nozzle chambers, especially with rotating liquid in them, are undesirable because of the wavering of the center-stream resulting from such flow-systems. Sharp (90°) joinings of channels and streams must also be avoided because of the turbulence and air bubble generation in such systems, which turbulence causes a unreliability and instability of operation. Although the nozzle chamber of FIG. 2 of U.S. Pat. No. 4,175,662 is rather close to the desired solution, nevertheless its reliability should be further improved, i.e such a new nozzle chamber should be developed where the reliability is practically 100% in order to reduce the stress that is developed in the operator by working with an equipment of relatively low reliability.

Therefore, the main object of this specification is to define a method of construction which, together with the other improved parts of the flow-system, is not only of a very high stability but also of a very high reliability, because due to the special inside wall geometry of said new chamber and channel system the formation of any air bubbles is practically impossible. This new analyser device is also improved in such aspects as sensitivity, maintenance, and operation, and extended in order to enable the use of epi- and direct-illumination of the particles flowing in the center-stream by means of lasers; these latter aspects have not been applied so far to the flow-systems similar to the one described in this specification.

DISCLOSURE OF INVENTION

On the basis of previous experiences the principles for the method of construction of the new analyser devices are as follows: The various streams flowing in the device are as short as possible in order to reduce to a minimum the possibility of turbulence development that follows from the Rayleigh-principle; streams join at the smallest possible angle; sharp (90°) stream deflections are avoided everywhere in order to avoid clogging of the channels which produce such deflections; the diameter of the center-stream is not very much larger than the cell (particle) diameter in order to provide for each particle the same analysing condition, regardless of its size, although if the volume of analysis is large enough the center-stream diameter can obviously also be larger; no sharp corners or edges are allowed in the flow-system, because they tend to tightly anchor air bubbles and such bubbles act like solid pieces of material and hence they divert the flow depending on their position and size in the flow-system. The nozzle chamber is, at least partially, of quasi rectangular crossection in order to prevent rotation of the sheath-stream liquid and it is tapered at its exit-end where its crossection is that of the exit-channel, where the various volumes of analysis are located; the walls of the nozzle chamber and also the walls of the other channels are of a nonreflecting and nonfluorescing black, either because said walls are coated or because the device is made of such a material. The exit-channel also serves to carry the particles in the center-stream from the analyser-part to the sorter-part of the device, if said parts are incorporated into the same device body; in the latter case the channel is called main channel. In general, any "necessary" obstacle in the way of the flow is of such streamlined shape that the split streams join, after passing said obstacle, without any appreciable turbulence, that is without so great a turbulence that would cause instability in the operation of the device. Each entrance-hole and exit-hole is as short as possible in order to make it possible to look into these holes with a simple microscope of low magnification and in order to be able to clean said holes from any dirt found in them occasionally; the said holes are connected to the corresponding containers by flexible (silicon) tubes; the said tubes are sealed at their entrance part by a screen-filter; the smallest dimension of the said filter openings is not larger than the smallest dimension of the cross-section of the flow-systems. The precautions described above enable the flow-systems of the analyser device to be sealed off permanently with a microscope cover glass; here as everywhere a nonreflecting and nonfluorescing black epoxy is used as gluing material.

Based on the principles of construction described above, a multiparameter particle (cell) analyser device has the form described below. Here a clear distinction is made between three entities. The first is the sensor, which converts one of the physico-chemical quantities (parameters) of a particle (cell) into an electrical impulse the amplitude of which is proportional to said property of the particle, whereby the said sensor's volume of analysis is located in the second entity, i.e. in the exit-channel of the analyser device; and the said second entity, in turn, is located inside the third entity, i.e. in the analyser equipment (apparatus), from which follows that the two latter entities are functionally interconnected through the first entity, i.e. the sensor or sensors for a multiparameter analyser equipment. The shape of the device body is preferably although not necessarily that of a rather flat cylinder in order to satisfy conditions for short entrance- and exit-holes; these holes enter at the bottom, and/or at the sides of the device where proper means are located by which the said device is attached to the analyser equipment; for the above reason the device-body diameter, too, is as small as possible; the material of the device is of some nonconducting and nonreflecting, nonfluorescing, black material, or at least all the active channel walls are coated with such a material. The analyser equipment, i.e. the third entity, houses in addition, the various optical, mechanical, and electro-optical devices which are necessary for the operation of said analyser equipment. The various active channels and the nozzle chamber are either carved or molded or manufactured in some other way into the smoothly polished top surface of the device body; the said channels are generally called active channels, because the combination of the various streams or the cell analysis or the cell sorting, if a sorter of the centerstream deflection type (see: T. Zöld, U.S. Pat. No. 4,175,662, op.cit.) is also incorporated in the analyser, takes place in these channels and cavities. The various volumes of analysis are located in the exit-channel, approximately at the downstream side of the joint of said channel with the exit of the nozzle chamber. Here the exit-channel should be so wide that a UV-objective of large numerical apperture and hence of large opening angle (about 120°) can "see" a cell moving in the center-stream, the said stream being situated approximately at the center of said channel, without being even partially obstructed by the side walls of said channel, because the fluorescent light, emitted by the cell, is collected by the large angle UV-objective. From the above description of the channel-system it also becomes clear that as the said channel-system is parallel to the cover glass and thus to the focal plane of the UV-objective, the center-stream can be easily directed to flow in the said focal plane; there is furthermore a possibility to carve the nozzle chamber in such a manner that said center-stream flows through said plane in an angle almost perpendicular to said plane. There is obviously no need for the cell to cross said plane perpendicularly; it is, however, a necessary condition for the correct analysis of the particles (cells) that their diameter is always smaller than the focal depth defined earlier. As the focal depth of objectives of large numerical apperture and magnification is very small, i.e. about 10 to 20 micron for an objective of numerical apperture (A=1.30), the cell must flow parallel or quasi parallel to said focal plane in the normal operation of the analyser and consequently the stability of the center-stream must be extremely high. For this reason the nozzle chamber according to this specification has been invented.

The said nozzle chamber is deepened (carved) into the top surface of the analyser device in the same manner as said exit-channel and is covered by the same cover glass as the latter; its top view is approximately that of an elongated oil droplet which is tapered at its connection to said exit-channel; its crossection is rather rectangular than circular. The nozzle is fixed into a nozzle holder and in this manner it can be easily taken out from the analyser device, i.e. from the nozzle chamber. The entrance hole for the sheathstream liquid (electrolyte) enters into the nozzle chamber at the bottom side of the upstream-end of the nozzle chamber with an angle between the nozzle and the nozzle chamber axis considerably smaller than 90° so that the sheath-stream liquid flows to the nozzle as it enters into the nozzle chamber at an angle of about 30°. Indeed, the nozzle is a considerable and necessary obstacle in the way of the sheath-stream liquid, and this is especially the case in the starting phase, when said chamber is empty. Therefore, in order to eliminate strong turbulence and the possible air bubble generation resulting from it, caused by the very nozzle in the starting phase, the joint of the entrance hole of the sheath-stream liquid and the upstream-end of the nozzle chamber is rounded off in such a manner that the nozzle chamber looks like a slightly bent continuation of the entrance hole. That is to say that although the entrance hole of the sheath-stream liquid can have any crossection at its beginning and at the outside of the device, nevertheless said crossection must gradually change to a quasi rectangular one and must have such a shape at its joint that it smoothly joins said nozzle chamber. Furthermore, in order to reduce the possibility of turbulence, and hence the air bubble formation at the entrance of the hole into the nozzle chamber, not only this joint is smoothed off, as described above, but also a filling of special shape is glued between the top side of the nozzle and the cover glass; the filling, however, is not glued to the nozzle but glued definitely to the upstream-end of the nozzle chamber and eventually to the cover glass, too, if and when the cover glass itself is glued to the surface of the analyser device. The special filling has such curved sides that they look like the front sides of an aircraft-carrier. By means of such a surface system, which is symmetrical to the symmetry plane of the device which is defined by the axis of the nozzle and that of the exit-channel, the two split streams of the sheath-stream liquid (split by the nozzle) are smoothly joined together as said liquid enters the nozzle chamber; another part of this liquid flows underneath the nozzle towards the exit-channel. The filling, however, has such a size that after some length of flow the split streams, which are now joined, and the lower stream-part envelop the nozzle completely and without turbulence before getting into touch with the liquid of the centerstream, the latter flowing out through the tip of the nozzle. As was described before in the BACKGROUND ART-SECTION, a stable center-stream could be achieved with such a chamber as the one drawn in FIG. 2 of U.S. Pat. No. 4,175,662, only if an air bubble did not develop in the starting phase defined earlier, where the special filling is treated in the new nozzle chamber. Therefore, the application of said filling is well justified. After its formation the center-stream flows into the exit-channel and carries the particles (cells) into the volume(s) of analysis, and after passing the said volumes the said stream flows either directly into a collecting waste bottle or into another device part such as a sorter device of the center-stream deflection type, described in U.S. Pat. No. 4.175.662 by T. Zöld; with this sorter the said analyser device is readily combinable.

The new analyser device described above can naturally be used in combination with the UV-microscope system with epi-illumination, as already described in connection with the flow-system of W. Dittrich and W. Göhde (see: op.cit.) by adjusting the analyser volume of said UV-microscope in the exit-channel of the device slightly downstream from the joint of the nozzle chamber and the said exit-channel. The considerable advantage of this flow-system, in addition to its very high stability and reliability, is that it is essentially nothing but an almost straight channel and therefore incomparably simpler than that of the device of W. Dittrich and W. Göhde, although the new device retains all the other good characteristics, such as the optical ones, which characterise the flow-system of said inventors (Dittrich and Göhde). If the said simple device is combined with the electrical sensor described in U.S. Pat. No. 4,237,416 by T. Zöld and further elucidated in FIG. 2 of U.S. Pat. No. 4,175,662, then another parameter, namely the cell (particle) volume can also be analysed; this device is henceforth called the combined analyser device.

Furthermore, another light source, namely a laser of UV-energy comparable to that of the said mercury lamp can be combined to said lamp in the "and/or"-combination through a number of mirrors and lenses of the standard type. The advantage of this laser, henceforth called the epi-laser, is that its spacially filtered and homogenized beam can be modified into a very thin and narrow ribbon-like beam, and if said beam is much thinner than the longitudinal dimension of the particle (cell) to be analysed, then only a small part, a slit, of said particle is illuminated by the beams, and if said particle is properly dyed (stained with a fluorescent substance), then the distribution of the dyed entity (DNA or protein) inside of said particle is obtained as said particle passes under the UV-objective. In this manner additional information is obtained about the cell structure. Naturally, such an analyser equipment with an epi-laser can be used with both the simple and the combined analyser device.

For excitation light energies of the order of one watt or higher can be used, but not the epi-illumination mode, because, as is known from experimental results, the heat sensitive material that fills up the space between the lenses of the UV-objective burns out at such energies, thus rendering the said objective useless for further work. In some cases, however, higher excitation light energy is necessary; this is the case in the analysis of many chromosomes and bacteriae, where the DNA amount is rather small and therefore higher excitation light energy is needed in order to get sufficient fluorescent light from the particles for the analysis.

Another variant of the above described device, both in its simple and its combined version, is obtained for this purpose by combining it with a high-power laser that illuminates the center-stream and hence the particles quasi directly by adjusting its spacially filtered and uniform beam into a channel-system that consists of two half cones with a common axis that is perpendicular to the optical axis of the said UV-objective and to the center-stream, i.e. to the exit-channel; the said half cones are carved into the top surface of the device in the same manner as the nozzle chamber and the exit-channel, so that the pointed ends of said half cones, which are located at both sides of the exit-channel, reach the vertical sides of said channel. From the previous description follows that said laser beam, henceforth called the direct-laser beam, the said optical axis of the UV-objective and the said center-stream form a quasi orthogonal axis system and from this aspect the new extended analyser device is similar to that of the jet analyser system; the important deviations, however, are the high stability and reliability of the center-stream and the possibility to use a UV-objective that is 10 times more powerful than the one used in the new extended analyser device. The said cones, henceforth called the light-channels, need not have a half-circular cross-section; their cross-section can be of quasi rectangular form as well. Their opening angle must be as large as possible in order to be able to collect the large-angle scattered light coming from the particle (cell) as it passes through the said direct-laser beam. The cross-section of both light-channels at the exit-channel should be of the order of $0.1 \times 0.1$ mm$^2$, in order to let the direct-laser beam pass through the exit-channel conveniently. The walls of the light-channels are of a nonreflecting and non-fluorescing black and are filled by a UV-transparent material, such as a high quality epoxy (one of which is known to be transparent down to 200 nm) or by a piece of quartz of the proper shape, or by a light-conducting fibre of the desired quality; the outside end of the light-channels is ground flat, polished, and a small piece of cover glass is glued to it with a high quality epoxy in order to provide an easily cleanable window for these channels. For direct-laser beams of very high power, quartz is used as filling and even the device body is made of metal in order to provide a better cooling of the device. From this follows that the laser beam coming from the said high-power direct-laser goes through one of the half cones (light-channels), then enters the exit-channel, crosses the center-stream and interacts with the particle (cell) in it. The result of this interaction is a partial scattering of said direct-laser beam where the small angle component can be separated from the persistent part of the beam as they leave the device through the other half cone (lightchannel); the small-angle scattering component is used for sizing the particle and if the particle (cell) is dyed, as was described before, then the large angle UV-objective gathers the fluorescent light coming from the cell if its analyser volume is adjusted to the crosspoint of the direct-laser beam and the center-stream. As this objective can gather about 10 times more fluorescent light from the dyed particle than the objectives used in the jet-system, this direct illumination system is correspondingly more sensitive than the jet-system, which is an improvement not negligible in small particle (cell, chromosome) analysis and sorting. The direct-laser itself, in this case, is mounted on an optical table together with the other parts of the analyser equipment and is naturally subject to the same safety regulations as the jet analyser system that also uses high power lasers.

As the beams of the epi-lasers and the direct-lasers are nearly perpendicular to each other, a so-called two dimensional slit-scan analysis can be carried out by simultaneously using both beam types, if both beams are of the shape of a very thin ribbon. In this manner additional information is obtained about the inside structure of the particle and by means of such double slit-scanning, cell lumps are often distinguished from deformed cells, which in some cases are cells of a cancerous type. (See: Wheeless, L. L. et al.: "False alarms in a slit-scan system etc. . . .", J. Histochem. Cytochem., vol. 27, pp. 596, 1979.)

As was mentioned previously in this section the flow-system of the new device(s) is so constructed that any part of the inside of it is clearly seen, either directly or through the cover glass that closes the channels at their top-side, regardless whether the said system is empty or whether electrolyte flows in it and any part of it is reachable by a mechanical device, such as a very thin wire or thread or by a water jet, and therefore any undesirable sold piece can be removed easily from the flow-system; the interior of the nozzle chamber in particular is easily reached because the nozzle is attached to the nozzle holder and thus both can be simply detached from the device body by simply pulling out the nozzle holder; through the opening thus created it is quite simple to remove dirt from the nozzle chamber. Therefore, the flow-system is permanently sealed at the end-phase of its construction with a cover glass using a non-reflecting and nonfluorescing black epoxy, and as the whole interior of the channel system has the same optical qualities, the background illumination and hence the signal-to-noise-ratio is considerably increased in comparison with the previous devices, where the cover glass is kept in its place at the top surface of the device by a ring of springs, additionally using vacuum-fat for a better closing of said channel system by said cover glass. Previous experience shows that this older procedure of channel covering is a rather unpractical one because it is cumbersome to place a well cleaned cover glass on the fatted top surface of the device; by gluing said cover glass permanently to said top surface, this cumbersome and straining operation is completely eliminated. The routine cleaning of the device, both inside and outside, is also easily done: the inside by rinsing the channel system with a lukewarm detergent which is made to flow through the flow-system for some time; the outside by rubbing the surface with a (Q-Tip) cotton-squab dipped into cleaning bezine, in order to remove the used immersion oil and other dirt. Thus, the overall maintenance of the new device(s) is considerably easier than that of the previous ones including those of the Dittrich-Göhde-Type.

One more important characteristic of the "top-side-transparent" channel-system lies in the fact that when the center-stream is dyed with black ink then said stream is clearly distinguishable from the surrounding sheath-stream under a stereo microscope and from this follows that the shape and size of said center-stream can be exactly observed from its beginning at the tip of the nozzle up to its end at the exit-hole(s), and can thus be adjusted to the proper cross-section by either adjusting the nozzle tip cross-section or by quenching the flow of the center-stream liquid outside the device; such a quenching, in turn, is done either by increasing the hydrodynamical resistance of the connecting (silicon) pipe or by reducing the level of the center-stream liquid (or suspension) in relation to the level of the sheath-stream liquid; very small pipe cross-sections must be avoided, however, as the tubes are easily clogged (blocked) at such cross-section.

The above description of the analyser equipment with three light sources shows that said system can be built up step by step, taking at first only a simpler analyser equipment with a mercury lamp and later attaching to it either one type or both types of the above mentioned lasers. This "domino-block" construction makes it possible for research groups with a very low budget to construct in the course of time a most complicated analyser equipment. Such a possibility may prove profitable even for the company pruducing such systems.

For large scale production of a prototype device, a molding procedure is suggested, because the depth of the flow-system is different at the various parts. Therefore, once a device of high quality has been developed and a large scale production is desired, the said device must be separated from the parts attached to its interior and then a negative is obtained from this remaining piece of the device for the molding process. With such a process the accuracy of the fine flow-system is preserved and the construction time of the device is considerably reduced, because the carving of the channel system is a very time consuming process.

POSSIBLE MODES FOR CARRYING OUT THE INVENTION

Figure 1A:
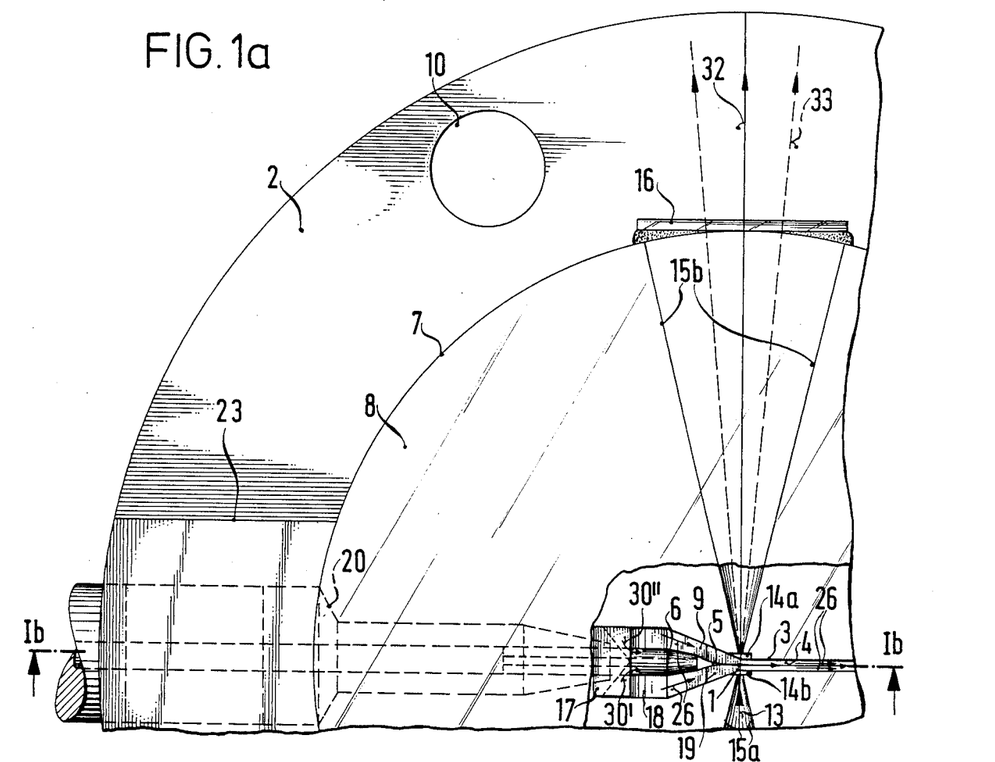
FIG. 1a and FIG. 1b represent the top view and the cross-section Ib respectively of a possible high stability analyser device.
Figure 1B:
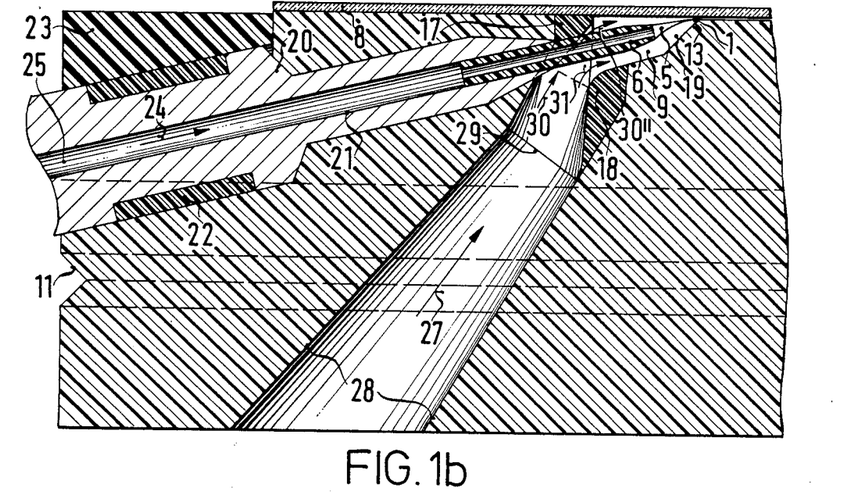

FIG. 1a and FIG. 1b show the top view and the cross-section 1b respectively through the symmetry plane of a possible practical, high stability and reliability device, where the symmetry plane is defined by the axis 1 of the device body 2 of cylindrical shape and by the center of the exit-channel 3 where the center-stream 4 also flows, which is the hydrodynamically focussed continuation of the center-stream liquid 5, which flows out of the nozzle 6. In this version, the device is of a double cylindrical shape with two main diameters wherein the diameter of the larger part is about 30 mm, and the diameter of the smaller part is about 18 mm, the latter defines the top surface 7 of the device. The use of the latter diameter enables the use of a standard microscope cover glass 8 that also has an 18 mm diameter. The cover glass 8 covers not only the exit-channel 3, but the nozzle chamber 9 (FIG. 1b) as well. The cover glass 8 is, in normal conditions, glued to the top surface 7 of the device, but in the initial construction phase of the device said glass can be pressed by a ring of fingerlike springs (not shown) to the top surface 7 by using three holes 10 (one of which is shown in FIG. 1a) and three screws. The shape of the device is that of a flat cylinder because its larger diameter is about 30 mm and its length (thickness) is only about 8 mm; from this follows that the various entrance and exit holes can be rather short as required by the principles of construction defined in the preceeding section of this specification. The material of the device body 2 should be preferably electrically non-conducting optically nonreflecting and nonfluorescing black. If such a condition can not be satisfied easily then hard plastic material can be used for the body. The walls of the active channels, defined earlier as cavities, where either the various streams are combined or where the particle (cell) analysis takes place, should be covered with a very thin layer of a material of the above defined quality; black epoxy was already found to be satisfactory for these conditions; naturally, the cover glass 8, too, should be glued with the same kind of epoxy to the top surface 7 in the final stage of construction. An approximately V-shaped groove 11 is cut into the lower, i.e. the larger diameter part of the device body 2, and by the help of this groove and three screws, located in the bayonet holder (not shown) the device can be fixed in the holder; this, in turn, is adjusted into that part of the analyser equipment by which the bayonet holder, and in this manner the device, too, can be shifted in the preferably horizontal x-y directions in such a manner that the device axis 1 coincides or at least is co-parallel to the optical axis of the UV-objective (not shown). In FIGS. 1a and 1b the ideal case is assumed, that the said two axis coincide with each other and are therefore both denoted by number 1. If the ideal construction is assumed for the sake of simpler description, then not only the center-stream 4 but also the optical axis 1 and the beam of the direct-laser 13 go through the orifice 12 of the device. In this case the direct laser enters the device from the right hand side of the center-stream 4. These three entities form a quasi orthogonal axis system at the orifice 12 of the device. Naturally, the exit channel 3 around the orifice 12 has to be UV-transparent not only through its top side, i.e. through the cover glass 8, but also through its two vertical sides; this is achieved by two windows 14a, and 14b, which can be made of the same material that fills the optical channels 15a and 15b; the other end of the optical channels is closed by a small piece of glass 16 (FIG. 1a) which is glued to the device body and to the end of said channel by the same UV-transparent filling that fills the channels. An epoxy of very high optical quality is known to be transparent down to 200 nm and is thus rather suitable for this purpose; a properly formed quartz wedge can also be used here. However, before the channels are filled up, the walls of these channels should be painted with a nonreflecting and nonfluorescing black material, preferably with the same black epoxy mentioned earlier, and then the filling should be ground and polished together with the top surface 7 of the device, and then the cover glass 8 should be glued to said top surface 7.

Obviously, in the above arrangement the UV-objective is perpendicular to the top surface 7 of the device and its focal plane, which is parallel to said surface 7 and hence the said focal plane can be adjusted with the use of a very fine screw into such a position that the center-stream 4 traverses the said focal plane diametrically. In accordance with the principles of the method of construction and of the general descriptions of the previous section for high quality analysis, two criteria are of very high importance, namely that the focal depth of the UV-objective should be larger than the cell (particle) diameter, and that the center-stream 4 should be in the focal plane at every start of operation and during every operation of the device; these are the "reliability and stability criteria". For cells and particles (chromosomes) of diameters up to 20 micron the second criterion (i.e. stability) is well satisfied by the ZEISS NEO-FLUAR 100/1.30, UV-objective, which is also used by Dittrich and Göhde in their system according to U.S. Pat. No. 3738,759; for diameters larger than the above mentioned, other objectives such as the NEOFLUAR 63/1.25 or objectives with an even smaller magnification than 63 should be used; such objectives have larger focal depths than the one mentioned first. It should be noted that objectives with a smaller magnification and a small numerical apperture are rather undesirable because they either gather less light or because their sight field quite large and hence the intensity of the excitation by epi-illumination is smaller, which leads to a poorer signal-to-noise-ratio which again reduces the quality of the analyser device. Therefore, whenever it is possible the high power NEOFLUAR 100/1.30 objective should be used and the flow-system be so constructed that the center-stream 4 is of an extremely high stability; this can definitely be achieved by the nozzle chamber described in the following part of this specification.

Without the fillings 17 and 18 as shown in FIG. 1a and FIG. 1b the nozzle chamber 9 has the shape of the bow of a rather primitive boat; its front part 19 has a pointed shape and its cross-section is adjusted to that of the exit-channel 3; in general, its cross-section is quasi rectangular; the important role of the filling is described below. The nozzle 6, which is usually made of a slightly flexible plastic tube for fine adjustment of its position, and hence for the adjustment of the center-stream in its proper position inside the sheath-stream, intrude at the high stream end of the nozzle chamber 9 and is held in the nozzle-holder 20, which is located at the long hole 21; a rubber or soft plastic (silicon) tube 22 provides an airtight but not a permanent sealing of said holder 20; a small piece of hard plastic material 23 is glued to the body 2 of the device in order to enable the drilling of the proper hole 21 for the nozzle-holder 20. As shown in FIG. 1a and FIG. 1b the entrance flow-system for the center-stream or suspension liquid 24 is rather simple; the said liquid is contained in an open container (not shown) and enters through a screen filter and a short (silicon) tube (also not shown in the figures) through the hole 25 and flows towards the tip of the nozzle 6 where, at first, it takes a conical shape 5, i.e. it is being focussed directly by the sheath-stream, represented in FIG. 1a, by the two flow lines 26, and indirectly by the pointed end 19 of the nozzle chamber 9. After this transition and due to its being surrounded by the sheath-stream 26, said fluid 5 is now converted into the center-stream 4, which carries the cells to be analysed to the orifice 12, i.e. to the volume(s) of analysis and after that either to an exit-hole or to a sorter device of the center-stream deflection type described in U.S. Pat. No. 4,175,622, 1979 by T. Zöld with which it is readily combinable.

While the flow-system for the center or suspension-stream 3 is rather simple this is not at all the case with the flow-system for the development of the sheath-stream, represented by two flow lines 26 in FIG. 1a and in fact, as previous observations indicate, all the troubles, i.e. the unreliability and the instability of other analyser equipments, arise from the improper way of enveloping the sheath-stream liquid 27 around the center-stream 4. In the previous device constructions for the correct method of flow-system construction for a highly reliable and stable cell analyser device. These principles are as follows: Channels and streams must join at a very small angle in order to reduce the generation of turbulence, and hence the generation of air bubbles to practically a zero value; such a generation can be very high especially in the starting phase where the empty flow-system is being filled up with electrolyte; no abrupt transitions are allowed for the change of channel cross-sections anywhere; sharp edges and corners are not allowed inside the flow-system because they tend to anchor air bubbles if any are generated; the cross-section of the nozzle chamber must be of quasi rectangular shape or when using additional filling material must be of such a form that permits the joining of streams at a turbulence-free small angle. In the following it will be shown that the flow-system for the sheath-stream liquid and for the sheath-stream itself satisfies the conditions stated above and for this reason the device of FIG. 1a and FIG. 1b is an analyser device of a high reliability and stability. FIG. 1b shows that the sheath-stream liquid 27 (usually either a pure physiological saline solution or distillated water) enters through the entrance hole 28 at an angle much smaller than 90° in relation to the axis of the nozzle 6; the said liquid is also filtered with a very fine screen filter and connected to the hole 28 by a flexible (silicon) tube; the latter two items are not shown in the figures. The sheath-stream liquid entrance hole 28 is preferably of a circular cross-section and of a decreasing diameter in order to increase the speed of the liquid flow; in general, the increase of the flow speed is desirable here because in this manner the small air bubbles of often obscure origin can be better washed out of the flow-system in this case, too; the said bubbles are known to stick rather strongly to any corner or sharp edge in the wall and they act as solid pieces, often causing considerable changes in the flow of the said liquid, so as to make the operation of the device impossible. Only a renewed filling of the flow-system with electrolyte can remedy the situation in such cases. After a short distance the hole 28 gradually changes from the circular to the rectangular form; in FIG. 1b this transition starts at the line 29, which is actually the projection of a half circle on the plane of the paper. The gradually decreasing cross-section of the remaining part of the hole 28 is constructed partly by carving the upper part of the circular hole into the quasi rectangular shape and partly by filling up the lower part with the lower-filling 18. For the further description of the flow of the sheath-stream liquid 27 we divide it theoretically into a lower part and an upper part, numbered 31 and 30 respectively. As shown in FIG. 1b the lower part of the stream 31 flows smoothly under the nozzle 6; on the other hand the upper part 30 is divided into two parts by the nozzle 6. These two half streams later join again smoothly at the upper part of the nozzle 6 through the joining effect of the upper-filling 17 at the top of the nozzle 6; the upper-filling 17 has the already described "aircraft-carrier-bow" shape which forces the said two stream parts to join at a small angle, as is shown by the flow lines 30' and 30" in FIG. 1a and 1b, instead of letting these streams collide in a "head-on" way. In previous devices which were devoid of a filling such as 17, a rather large air bubble developed at that volume where now the filling 17 is located, almost in each starting phase, i.e. when the flow-system is filled up with electrolyte under the suction effect of a pump attached to the exit of the system. Obviously, the development of such bubbles was due to the "head-on" collision of the two stream parts. When such a bubble was observed in the said place, the operation of the flowsystem was found to be unacceptable; however, in the absence of such an air bubble, center-stream diameters as small as one micron have been observed under a stereo-microscope of a 50-fold magnification; the said stream, dye-contrasted by black ink, was not found to waver at all. This means that with a flow-system as shown in FIGS. 1a and 1b an analyser device of high reliability and stability can be constructed. To go on with the description of the various partial streams, i.e. streams 30', 30" and 31, it is important to note that these streams must join and surround the nozzle 6, well before reaching the tip of it. Indeed, it is only in this way that the actual sheath-stream, which is represented by the flow line 26, was correctly formed and subsequently focussed hydrodynamically, the conical part of the center-stream 5 into a stable and uniform center-stream 4 which carries the particles to the volume(s) of analysis, i.e. to the orifice 12. Furthermore, it is desirable, although not necessary, to adjust the cross-section dimensions of the exit-channel 3, i.e. width and depth, to be proportional to those of the pointed part of the nozzle chamber 19 (FIG. 1b), because only in such a case will the cross-section of the center-stream 4 have the cylindrical form, provided that the exit-hole of the nozzle 6 also has a circular form this fact is the consequence of the laminar flow in the pointed part of the nozzle-chamber 19 and in fact of that in the whole flow-system. Center-streams of other cross-sections are made by adjusting the geometry of the exit of the nozzle 6 correspondingly; for instance, while stream cross-sections of the circular form are well suited for round or long cells (particles), ribbon-like center-streams are very useful to orient flat cells into the horizontal or vertical position if the cross-section of the center-stream 4 is comparable to that of the particles (cells). Fine adjustment of the center-stream cross-section can also be made externally through a change of the hydro-dynamical resistance in the connecting tube for the center-stream liquid. Laser beams of the ribbon form, which are perpendicular to the flow of the particle, are very suitable in such cases for one or two dimensional slit-scanning or for multiplexing (see: Severin et al., op.cit.) if the two lasers illuminate the same part of the center-stream 4 or different parts of it. As the stable center-stream 4 always flows in the focal plane of the UV-objective, the particle, too, flows in that plane and in this way, the optimum condition is possibly achieved both for the illumination and for the adjustment of the UV-objective, which is a considerable advantage in comparison with the known flow-system previously described.

From the above description and from the description of the previous section follows that the optical axis of the UV-objective 1, assumed here to coincide with the center axis of the analyser device and therefore also denoted by 1, is perpendicular to the top surface of the device 7 and hence to the center-stream 4. The direct laser 13 is also quasi perpendicular to the said axis. Thus, as was said before, the said three axes form a quasi orthogonal axis-system. Naturally, more than one epi-laser and/or direct lasers can be attached to the same analyser equipment; in the case of two direct lasers one of them must be placed at one side and the other at the other side of the simple analyser equipment, and the beams must be slightly tilted in relation to each other in order to avoid the undesirable combination of the persistent and scattered parts of the beams, which are numbered 32 and 33 in FIG. 1a. As was said above, the beam of the direct laser can be used as excitation source for fluorescence analyses if the particles are dyed with some fluorescent substance and/or the small angle (up to about 2°) forwards scattered part 33 of the primary laser beam 13 can be used for particle sizings.

FIGS. 1a and 1b show that the maintenance of the device is also very simple. The various cavities such as the nozzle chamber, the entrance and exit-holes (the latter is not shown) are easily observable, partly because of the transparent top side of the device, partly because the holes usually have a larger diameter than one mm; by pulling out the nozzle holder 20 the inside of the nozzle chamber 9 not only becomes better visible but any part of it is reachable either with a thread or with a jet of water in order to clean out some debris; the latter, however, occurs rather seldom because the mentioned filters are already placed (mounted) at the entrance of the tubes for the two liquids 24 and 27. On this occasion the nozzle 6, too, can be observed, adjusted or even replaced by another one; center-stream cross-sections can be quickly changed in this manner. If the device is only an analyser device then the exit-channel 3 must be as short as possible in order to reduce the probability of clogging; if the analyser is combined with a sorter of the center-stream deflection type then the exit-channel (then called "main-channel") is about 1 to 3 mm long; this part can also be seen and can be reached with the means described above or the debris can be sucked out easily. Once said debris is in the nozzle chamber 9, it can be easily removed from it. The cleaning of the outside of the device is also easy because all the surfaces of the device are smooth and easily cleanable even with a Q-Tip. The cover at its exterior side must be cleaned occasionally with cleaning benzine in order to wash off the unwanted immersion oil, while the inside of the flow-system must be cleaned with some detergent by letting it flow through the whole flow-system for some time. As there is no need to remove the cover glass, all the maintenance operations are easily carried out from the outside and for this reason the fear of clogging is considerably reduced, which is a great advantage of this system in comparison with others, where the replacement of the cover glass is a rather tedious and straining operation.

Figure 2A:
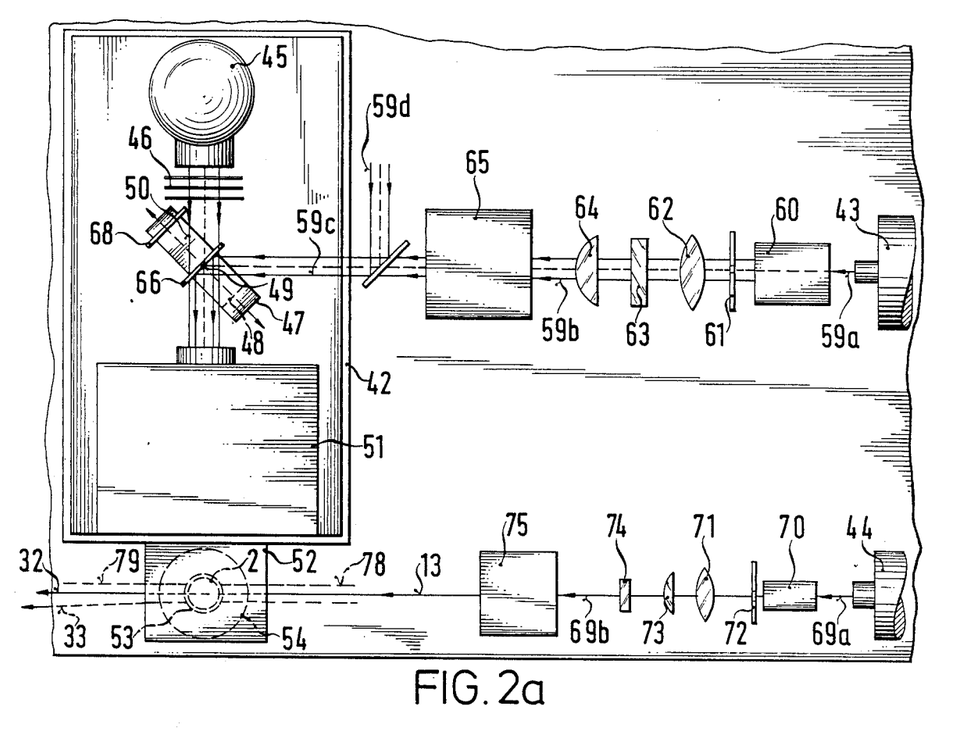
FIG. 2a and FIG. 2b represent the top view and the front view respectively of an analyser-system with the three main light sources.
Figure 2B:
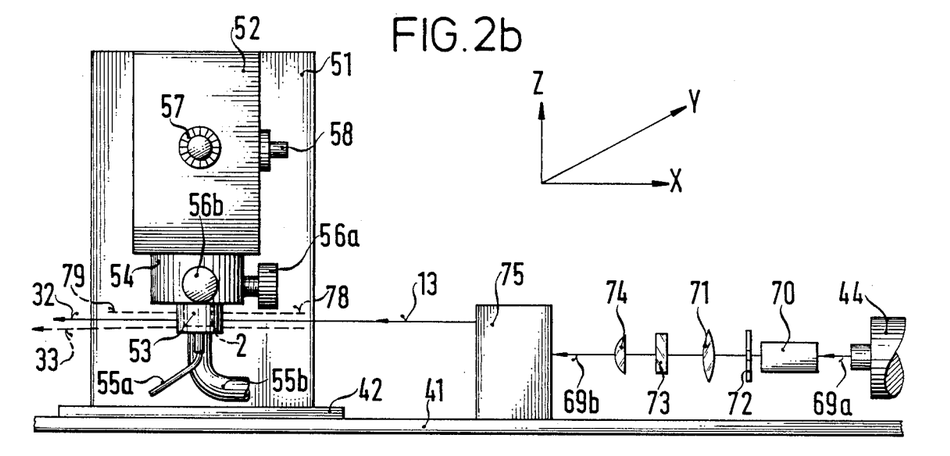

FIGS. 2a and 2b show the top and front-views of the analyser-system, respectively, as it is situated on an optical table 41. The main parts of this system are the analyser-equipment 42 (in doubly lined rectangle), the epi-laser 43, and the direct laser 44. (The x-y-z coordinate system helps to define the various directions.) Thus, while the coordinate axes x and y lie on the optical table 41, and therefore also in the plane of FIG. 2a, the axes x and z lie in the plane of FIG. 2b, and the direction of the z-axis is identical with the vertical direction. The analyser-equipment 42 is divided into five main parts. These are the high pressure mercury lamp 45 of 100 Watt power (FIG. 2a), which through a collector lens (not shown), situated in the lamp housing, and after filtration by a system of optical filters 46 provides about 10 mWatt power in the UV-range. If the mirror slider 47 is in such a position that the dash-lined part 48 of said slider is at the beam crossing 49, then the filtered UV-beam 50 enters into the first closed box 51, where two lenses and at least one photomultiplier are located; the latter will be closer described in this text. One of the said lenses is an adjusting lens for the Koehler's-optic and serves to project at least part of the mercury arc of said lamp into the proper position which is necessary for the correct illumination for the Koehler's-optic, which itself consists of the other lens and of the UV-objective. The UV-objective (not shown) is located inside the second closed box 52 and can be adjusted by a very fine screw along the vertical (z) axis in order to position its focal plane in such a manner that the center-stream, defined earlier, flows in this focal plane. The analyser-device 2, where the center-stream and the cells to be analysed flow is located in the bayonet holder 53 (FIG. 2b) together with the entrance tubes for the suspension and sheath-stream liquids, numbered 55a and 55b, and is shown with dashed lines 2; the analyser device, however, is indicated with a dashed circle in FIG. 2a. The bayonet holder 53 is fixed into a small microscope table of disc shape which is located in the light-tight cylinder 54; the said small table and thus the analyser device, too, can be slid horizontally, i.e. in the x-y plane, by the fine screws 56a and 56b which move the device along the y and x axes, respectively. With these two screws the orifice, which is indicated by 12 in FIGS. 1a and 1b, can be adjusted right under the UV-microscope, which, as was said above, can be slid vertically by a very fine screw for optimal adjustment. If the device is a sorter device, described in U.S. Pat. No. 4,175,662 by T. Zöld, then with the use of the fine screws 56a and 56b the whole length between the orifice and the channel branching can be observed conveniently, because by the epi-illumination the light source moves together with the sight field of the UV-objective. Indeed, objects in the sight field of the UV-objective can be seen either because they reflect part of the UV-spectrum or because they are dyed with a substance which is fluorescing only if its molecules are combined with some well specified molecules, such as DNA or protein of the cell; part of the reflected or fluorescent light is collected by the UV-objective and can be seen through the eyepiece 57 (FIG. 2b) if the flip-mirror 58 is turned 45° relative to the optical axis of the microscope to which the UV-objective also belongs; in the other position of the flop-mirror 58 the said mirror is out of way of the collected light and thus the light is absorbed by the cathode of the photomultiplier (mentioned earlier) located in the first box 51 and is converted into electrical energy. Thus, as the properly dyed cell passes under the UV-microscope, a fluorescent light is generated, which is converted into an electrical impulse in said photomultiplier and processed further in the electrical equipments connected to this photomultiplier. For the process described above the conventional version of the analyser-equipment, i.e. the one without the mirror slider 47, called an Impulse-Cyto-Photometer or ICP, can be used although the other optical analyser-equipments described in the BACKGROUND ART, which function in the same way, could also be designated as ICP analysers. Hereafter the designation "analyser-equipment" 42 will be used in order to distinguish the equipment with the mirror slider part 47 described here from the conventional ICPs, which do not have these parts.

The mirror slider 47 is incorporated into the analyser-equipment in order to enable the combination of the beam 59a of the epi-laser 43 with the UV-light 50 of the mercury lamp 45. This is a new type of beam combination. The epi-laser 43 with its various beam shaping devices is shown only in FIG. 2a. The "raw" epi-laser beam 59a first enters into the spacial filter 60, in order to be cleaned from the spurious modes of the laser beam and in order to obtain uniform light distribution over its beam cross-section; the spacial filter 60 can also be a beam expander or a beam diameter reducer if that should be necessary in a particular case; it is known from general experience that such a filter 60 is necessary in any case when a very high quality laser beam is desirable as an end product. The horizontal slit 61 (indicated only by a dashed line), the biconvex lens 62 and the two cylindrical planconvex lenses 63 and 64, are necessary in order to obtain an epi-laser beam of the desired cross-section. In the conventional case where only a horizontal, i.e. x-directional beam of circular cross-section is needed, in addition to the spacial filter and beam expander 60 only the biconvex lens 62 is necessary in order to obtain a beam of about 15 mm diameter 59b which can be shifted in the y and z directions with the beam shifter 65, in order to obtain beam 59c, which is coaxial with the beam 50 of the mercury lamp 45. These two beams can be combined and subsequently projected into the first closed box 51 if the dichroic mirror 66 of the mirror slider 47 is shifted into the beam cross-point 49. With another dichroic mirror 67 two epi-laser beams, i.e. beams 59c and 59d, of different UV-light spectrum bands can be combined. If the epi-laser beam 59d is to be connected alone to the analyser-equipment 42 then the mirror 67 should be a total-reflecting one and in this manner the epi-laser beam 59d with the described additional beam shaping devices, must be placed on a common rigid and heavy frame, as was described in the previous section in order to obtain a cell analyser-system of the desk-set type without using a very expensive optical table.

On entering the first closed box 51 the epi-laser beam follows the same path as was described already above for the beam of the mercury lamp. Naturally, the beam intensity can not be higher than of the order of 10 mWatt in order to avoid damage to the material that fills the space between the lenses of the UV-objective. The two beams mentioned above reach the objective after being reflected by a dichroic mirror located in the second closed box 52; this mirror must have such a cut-off wave length that it reflects the UV-beams into the UV-objective but lets through the fluorescent light spectrum emanating from the cells which are illuminated by the UV-beams. Obviously, the UV-objective in this optical system is both the condenser lens for the Koehler's-illumination optics and also the objective of a microscope that gathers the fluorescent light emanating from the cells (particles) that can be seen either through the eyepiece 57 or can be collected by the cathode(s) of the photomultiplier(s) attached to this microscope system. If the totally reflecting mirror 68 is at the beam cross-section 49 instead of the dichroic mirror 66, then only the beam of the epi-laser 59c and/or 59d enter(s) the analyser part of the equipment; in any case, when this beam is used then it is desirable to adjust the laser beam 59c of uniform circular cross-section with the lens 62 in such a manner that said beam is still quasi uniform when it illuminates the cell (or another object). The lens 42 is clearly desirable because there are only three lenses in the two closed boxes 51 and 52 (the UV-objective included) and from simple geometrical optics follows that a beam of uniform cross-section can be transferred through a number of lenses and will be of uniform cross-section only if the number of lenses is even; lens 62 is the fourth lens in the path of the epi-laser beam and thus gives an even number of lenses.

With the highly purified laser beams cross-sections of very small size can be obtained. As was described earlier, a ribbon-like beam is required for slit-scanning which must be thinner than the longitudinal dimension of the particle to be analysed. Such a beam can be obtained from the laser beam 59a if a horizontal slit 61 is placed into the path of the filtered and homogenized beam; lenses 63 and 64 are needed only if the beam is to be squeezed additionally in the z or y-direction (see: Wheeles, L. L. et al., op.cit.). The horizontal laser beam 59b or 59c with its flat side, too, directed horizontally is projected into the analyser part, and after being reflected by the dichroic mirror, which is located directly before the objective, it takes the vertical (z) direction with its flat side perpendicular to the center-stream, which is flowing in the positive y-direction. Thus, if said beam is thin enough in comparison with the longitudinal dimension of the particle (cell, chromosome) to be analysed then only a thin cross-section of said particle is illuminated and analysed because the UV-objective can gather fluorescent light only from that part of said particle which is illuminated by the UV-excitation beam of the epi-laser of the band form. Because of its "epi" nature it is very easy to work with such a system, because the illumination of the particle and the gathering of the fluorescent light is adjusted by the same means, i.e. by the fine screws 56a and 56b together with the fine screw (not shown) for the vertical adjusting of the UV-objective.

If the particle to be analysed is so small that the illumination neither from the mercury lamp nor from the epi-laser is strong enough then the direct laser 44 must be used as light source for this type of analysis. Its beam 69a is spacially filtered by the filter 70 in the same manner as for the epi-laser and is adjusted by the biconvex lens 71 or shaped by the vertical slit 72, and/or by the cylindrical planconvex lenses 73 and 74, in order to obtain the beam 69b which can be shifted into such a position by the beam shifter 75 that the final direct-laser beam 13 (identical with beam 13 of FIGS. 1a and 1b) enters through a small hole into the bayonet holder 53 and eventually into the analyser (sorter) device 2, shown in detail in FIG. 1a. Upon reaching a cell in the center-stream (denoted by 4 in FIG. 1a) which flows in the positive y-direction, the direct-laser beam 13 is divided into a quasi persistent and a scattered part, i.e. 32 and 33, respectively (as is shown in FIG. 1a). If the beam 13 is of the circular cross-section then its diameter varies, approximately, between 0.02 and 0.2 mm depending on the size of the cell or particle to be analysed. Correspondingly, the cross-section of the exit-channel (3 in FIG. 1a) should also be adjusted to the size of the largest particle flowing in the center-stream. Slit-scanning can also be carried out with this beam if its form is that of a horizontal ribbon with its flat side directed vertically, i.e. in the z-direction; in such a case, too, as in the case of the epi-laser, the beam should be much thinner than the longitudinal dimension of the particle to be analysed. A directlaser beam of such a form is achieved by means of the slit 72 and/or the planconvex cylindrical lenses 73 and 74 which focus the originally cylindrical beam along the y and z-axes in order to obtain a ribbon-like beam of vertical direction which is also perpendicular to the center-stream.

Naturally, the epi-laser and the direct-laser beams of the ribbon form can be used simultaneously in order to carry out two-dimensional slit-scanning. In this manner cell lumps can be distinguished from deformed cells which are often of cancerous type.

As both laser beams are of the UV-type and are consequently dangerous for the human eyes, all the beams must be covered with such tubes that are either only semi-transparent or are not transparent at all. The small tubes 78 and 79 attached to both sides of the bayonet holder 53 are especially useful for this purpose, because the various other parts of the analyser-equipment, such as the eyepiece 57, the fine screws 56a and 56b and the entrance tubes 55a and 55b, etc., which are in the visual field of the operator of the analyser-system, are located around this part.

I claim:

1. A device for carrying out a method for generating a stream combination, composed of a very thin center stream of electrolyte with particles suspended in it and a hollow stream of usually transparent electrolyte, which envelops said very thin center stream, in a completely closed, streamlined flow chamber, which is free of air bubbles after a filling-up phase in which said chamber is filled-up by the two streams from which said fluid stream combination is composed, said device comprising:

a body;
   a tube forming a nozzle within said body for leading a center-stream liquid coaxially into a chamber of said nozzle, said nozzle chamber having smooth, hydrophilic and streamlined curved inside walls so that said chamber is turbulence-free, a large part of the chamber being occupied by said nozzle; an entrance channel joined to said chamber so as to lead the liquid for the enveloping stream into said chamber with a small angle between the enveloping stream and the nozzle, so that the nozzle splits the entering enveloping stream into three partial streams including one partial stream flowing underneath the nozzle and two partial streams flowing around the nozzle, said entrance channel having a cross-sectional shape substantially the same as that of said chamber at a point where said chamber and said entrance channel are joined;
   a surface combination included at the top of the nozzle, said surface combination having a concave-sided wedge-shape, and being tightly fitted against the nozzle so as to force said two partial streams flowing around the nozzle to reunite at a small angle and be parallel to the nozzle; and
   the inside walls of said chamber being formed so as to reunite said three partial streams at a small angle with respect to each other and to wrap around the nozzle so as to form a hollow turbulence-free stream, so that said hollow stream sweeps bubbles out of the chamber and fills up a space between said nozzle and the walls of said chamber completely and in an air-bubble-free manner;
   said nozzle having a tapered top so as to allow the reunited streams to form the hollow stream which envelopes the very thin center stream and focuses it hydrodynamically at a pointed part of the wedge-shaped surface combination as said stream combination leaves said chamber, so that a stable thin center-stream is reliably obtained.

2. A device according to claim 1 wherein the center-stream has a cross-section which is adjustable to any size and shape by a cross-sectional form of a tip of the nozzle cross-section adjustments of hydrodynamical resistance in an external part of the flow of the center-stream being applicable so as to make fine adjustments of the center-stream.

3. A device according to claim 1 or 2 wherein the entrance channel for the enveloping-stream starts with a cross-section of circular form, which is gradually transformed into an approximately rectangular form proportionally to the cross-section of said nozzle chamber, wherein the channel cross-section gradually decreases to that of said chamber at the joining of said channel to said chamber, at a rear of said chamber, wherein said joining is rounded off and corners are filled up with an epoxy-like material so that sudden changes in the cross-section are avoided, and wherein said chamber cavity is a slightly bent continuation of said channel for the enveloping-stream, so that said transition and cross-section shape prevents said liquid from rotating in said flow-system.

4. A device according to claim 1 wherein the cavity of the nozzle chamber and other channels are carved into a very flat and smooth surface of the device body and wherein a thin microscope cover glass is included to cover said chamber and channels, which is transparent even to UV-light, so that the nozzle chamber and the channels form an air tight flow-system.

5. A device according to claim 4 wherein at least the surfaces of the carved cavities of the device body are either one of a non-reflecting and nonfluorescing black plastic and, if considerable heat is to be dissipated by the device body, some metal having the same optical properties as said plastic, and wherein said cover glass is also glued to said top surface with the same material.

6. A device according to claim 1 wherein said device body is of such a minimal diameter or extension, perpendicularly to the axis of the body, and entrance and exit holes, drilled into said body are so short that their interior can be seen clearly through a common microscope of relatively low magnification and wherein said holes join to said channels or at a very small angle such as about 30°.

7. A device according to claim 1 wherein a hollow nozzle is mounted at the nozzle holder of, which can be pulled out from said device body.

8. A device according to claim 1 wherein the nozzle includes a holder which is a hollow cylindrical piece having an up-stream end at which a flexible tube is connected which has an up-stream end equipped with a filter system, the filter system having micro openings not smaller than a largest particle of a suspension to be processed.

9. In an analyzer device of the type for use with a particle analyzer system, said device for the counting of particles suspended in a liquid electrolyte according to preselected properties such as particle size, DNA, and/or protein amount, as they flow in a thin center-stream, which is enveloped by a clear and particle free sheath-stream, through the various volumes of analysis where they interact through some of their physico-chemical properties with a sensor of said device and where, to the magnitude of the quantity to be analyzed, corresponds an electrical impulse which is proportional to said magnitude, the improvement further comprising:

(a) stream combining means incorporated into said analyzer device body, said stream combining means including:

(i) a tube forming a nozzle within said body for leading a center-stream liquid coaxially into a chamber of said nozzle, said nozzle chamber having smooth, hydrophilic and streamlined curved inside walls so that said chamber is turbulence-free, a large part of the chamber being occupied by said nozzle; an entrance channel joined to said chamber so as to lead the liquid for the enveloping stream into said chamber with a small angle between the enveloping stream and the nozzle, so that the nozzle splits the entering enveloping stream into three partial streams including one partial stream flowing underneath the nozzle and two partial streams flowing around the nozzle, said entrance channel having a cross-sectional shape substantially the same as that of said chamber at a point where said chamber and said entrance channel are joined;

(ii) a surface combination included at the top of the nozzle, said surface combination having a concave-sided wedge-shaped, and being tightly fitted against the nozzle so as to force said two partial streams flowing around the nozzle to reunite at a small angle and be parallel to the nozzle; and (iii) the inside walls of said chamber being formed so as to reunite said three partial streams at a small angle with respect to each other and to wrap around the nozzle so as to form a hollow turbulence-free stream, so that said hollow stream sweeps bubbles out of the chamber and fills up a space between said nozzle and the walls of said chamber completely and in an air-bubble-free manner; and (iv) said nozzle having a tapered top so as to allow the reunited streams to form the hollow stream which envelopes the very thin center stream and focuses it hydrodynamically at a pointed part of the wedge-shaped surface combination as said stream combination leaves said chamber, so that a stable thin center-stream is reliably obtained;

(b) means to incorporate said analyzer device into an analyzer-system where other optical and electro-optical parts of said sensor are located;

(c) said device including an exit channel, a part of the exit-channel being UV-transparent not only at a side and which is covered with a cover glass, but also at a part of its vertical sides for providing the possibility of simultaneous multiple illumination of said particles of said center-stream by more than one laser; and (d) a channel-system, including two half cones of arbitrary cross-section geometry, having a common axis and pointed against each other and reaching with their pointed ends said exit-channel on both sides of it where said UV-transparent sides are also located, said two half cones being filled with a UV-transparent material and being closed at their outer ends with a small piece of thin glass.

10. An analyzer device according to claim 9 wherein when a very high power laser beam is used, said channel-system, operating as optical-channels, is filled up with a very heat resistant and UV-transparent material, and one of the device body and a coating of the walls of the optical-channels is a of a metal having good optical qualities, such as nonreflecting and nonfluorescing black.

11. An analyzer device according to claim 10 wherein the body, which incorporates various channels and holes, is of a flat cylinder form made of one of plastic and metal that is neither reflecting or fluorescing at any part of the optical spectrum, the flat cylinder having one flat side that is finely polished; and wherein the channel walls are of required optical quality, and wherein the top side of the channels and holes is closed by a UV-transparent microscope cover glass or quartz glass, and wherein a gluing material of the required optical quality glues the cover glass to the top side.

12. An analyzer device according to claim 9 wherein the exit-channel defining the exit for said nozzle chamber, houses various volumes of analysis at a part downstream from the exit of said nozzle chamber.

13. An analyzer device according to claim 12 wherein all channels and streams or stream-parts join at a small angle and all said channels and holes vary without any sudden change in their crosssections.

14. An analyzer device according to claim 13 wherein a UV-microscope with an objective of very high magnification and with maximum numerical aperture but with very flat volume of analysis is adjusted into said exit-channel in such a manner that the center-stream, and the particles to be analyzed, flow in the working-plane phase, through the sight field of said objective diametrically, the focal depth of said objective being always larger than the diameter of the largest particle of the suspension to be analyzed.

15. An analyzer device according to claim 14 wherein at least one laser beam is combined with a conventional high pressure mercury lamp, which also works in the epi-illumination mode.

16. An analyzer device according to claim 9, wherein said channel-system is an optical-channel which comprises a laser beam of very high power for the illumination of the particles flowing in the center-stream.

17. An analyzer device according to claim 9, wherein the three light sources are used simultaneously.

18. An analyzer device according to claim 14 wherein said nozzle chamber is carved at its front part so that particles cross said sight field at an angle smaller than 90° with respect to the said field.

19. An analyzer device according to claim 13 wherein the inside of the various channels and holes are observable through a common microscope.

20. An analyzer device according to claim 13 or 19 wherein the device body is dimensioned and said channels, cavities and holes join at a very small angle so that the whole flow-system is easily observable through a common microscope, so that even with said cover glass being glued being glued permanently to said polished surface of the device, any part of said flow-system can be reached by any of a very thin wire a plastic thread and a water jet.

21. In an analyzer-system of very high reliability and stability for analyzing and sorting, depending on the type of device incorporated in said apparatus, particles suspended in a liquid electrolyte, said improvement comprising:

(a) an analyzer device including:

(A) stream combining means incorporated into said analyzer device body, said stream combining means including:

(i) a tube forming a nozzle within said body for leading a center-stream liquid coaxially into a chamber of said nozzle, said nozzle chamber having smooth, hydrophilic and streamlined curved inside walls so that said chamber is turbulence-free, a large part of the chamber being occupied by said nozzle; an entrance channel joined to said chamber so as to lead the liquid for the enveloping stream into said chamber with a small angle between the enveloping stream and the nozzle, so that the nozzle splits the entering enveloping stream into three partial streams including one partial stream flowing underneath the nozzle and two partial streams flowing around the nozzle, said entrance channel having a cross-sectional shape substantially the same as that of said chamber at a point where said chamber and said entrance channel are joined;

(ii) a surface combination included at the top of the nozzle, said surface combination having a concave-sided wedge-shape, and being tightly fitted against the nozzle so as to force said two partial streams flowing around the nozzle to reunite at a small angle and be parallel to the nozzle; and (iii) the inside walls of said chamber being formed so as to reunite said three partial streams at a small angle with respect to each other and to wrap around the nozzle so as to form a hollow turbulence-free stream, so that said hollow stream sweeps bubbles out of the chamber and fills up a space between said nozzle and the walls of said chamber completely and in an air-bubble-free manner; and (iv) said nozzle having a top so as to allow the reunited streams to form the hollow stream which envelopes the very thin center stream and focuses it hydrodynamically at a pointed part of the wedge-shaped surface combination as said stream combination leaves said chamber, so that a stable thin center-stream is reliably obtained;

(B) means to incorporate said analyzer device into an analyzer-system where other optical and electro-optical parts of said sensor are located;

(C) said device including an exit channel, a part of the exit-channel being UV-transparent not only at a side and which is covered with a cover glass, but also at a part of its vertical sides for providing the possibility of simultaneous multiple illumination of said particles of said center-stream by more than one laser; and (D) a channel-system, including two half cones of arbitrary cross-section geometry, having a common axis and pointed against each other and reaching with their pointed ends said exit-channel on both sides of it where said UV-transparent sides are also located, said two half cones being filled with a UV-transparent material and being closed at their outer ends with a small piece of thin glass;

(b) a conventual UV-microscope, equipped with a conventional high pressure mercury lamp and a Koehler's optic for the homogeneous illumination of an object in the epi-illumination mode, and using at least one photomultiplier in order to convert fluorescent light that is emitted by the cell and collected by said UV-objective of the microscope into an electrical impulse;

(c) in combination with said mercury lamp, one or more lasers, combined with said lamp through use of mirrors and lenses, also in the epi-illumination mode; and (d) at least one laser of very high energy in the direction illumination mode.

22. A method for generating a stream combination, composed of a very thin center stream of electrolyte with particles suspended in it and a hollow stream of usually transparent electrolyte, which envelopes said very thin center stream in a completely closed, streamlined flow chamber, which is free of air bubbles, after a starting phase in which said chamber is filled-up by the two streams from which said fluid stream combination is composed, so that after the starting phase a steady flow-phase is created where said very thin stream has the same shape and is at the same position relative to the outlet of said flow chamber where it leaves said chamber, said method having the steps of:

allowing the fluid of the very thin stream to enter through a hollow intrusion into a rear end of the flow chamber;

providing said chamber with smooth, hydrophilic and streamlined inside walls;

providing liquid for the enveloping stream to enter into the rear end of flow chamber in the form of a rotation-free, thick stream having a cross-section at least as large as that of said chamber at the same place;

forming an upstream half of said intrusion as a wall which suppresses the rotation of the enveloping stream, the angle between said intrusion and said thick stream being smaller than 90°;

splitting and thick stream into three parts by said hollow intrusion and then constraining said stream parts by the walls of said cavity and by the surface of the intrusion to reunite later, at a small angle with respect to each other and to said intrusion, and to flow further surrounding and touching said intrusion, so that the thus formed hollow stream fills up the space between said intrusion and the walls of said chamber gradually;

causing the thick stream to flow, especially at the starting phase when said chamber is empty of all kinds of fluid, at a rate so that all possible air bubbles are swept out of said cavity through its outlet, so that, at an end of the starting phase, the chamber is filled up completely with air-bubble-free fluid;

joining, at the tip of said intrusion, the fluid of the very thin stream as the latter enters into the chamber at a practically zero angle with respect to said thick stream; and hydrodynamically focusing the fluid of the very thin stream by said enveloping stream so that said thin stream has the same form and the same position relative to the outlet of said chamber at the end of each starting phase.

* * * * *